United States Patent
Lee

(10) Patent No.: US 10,207,266 B2
(45) Date of Patent: Feb. 19, 2019

(54) MICROFLUIDIC DEVICE FOR DETECTING CELLS OF BLOOD

(71) Applicant: FOXCONN INTERCONNECT TECHNOLOGY LIMITED, Grand Cayman (KY)

(72) Inventor: Genn-Sheng Lee, New Taipei (TW)

(73) Assignee: FOXCONN INTERCONNECT TECHNOLOGY LIMITED, Grand Cayman (KY)

( * ) Notice: Subject to any disclaimer, the term of this patent is extended or adjusted under 35 U.S.C. 154(b) by 272 days.

(21) Appl. No.: 14/869,942

(22) Filed: Sep. 29, 2015

(65) Prior Publication Data
US 2017/0087550 A1    Mar. 30, 2017

(51) Int. Cl.
| | | |
|---|---|---|
| *B01L 3/00* | (2006.01) | |
| *G01N 35/00* | (2006.01) | |
| *G01N 1/10* | (2006.01) | |
| *G01N 15/06* | (2006.01) | |
| *G01N 33/00* | (2006.01) | |
| *G01N 33/48* | (2006.01) | |
| *G01N 33/72* | (2006.01) | |
| *G01N 15/10* | (2006.01) | |

(52) U.S. Cl.
CPC .... *B01L 3/502715* (2013.01); *G01N 15/1031* (2013.01); *G01N 15/1056* (2013.01); *B01L 2200/027* (2013.01); *B01L 2200/0647* (2013.01); *B01L 2200/12* (2013.01); *B01L 2300/041* (2013.01); *B01L 2300/0645* (2013.01); *B01L 2300/0877* (2013.01); *B01L 2300/0883* (2013.01); *G01N 2015/1006* (2013.01)

(58) Field of Classification Search
CPC .......... B01L 3/00; G01N 35/00; G01N 33/72; G01N 33/48; G01N 1/10; G01N 15/06; G01N 33/00
USPC .... 422/50, 68.1, 81, 82.01, 82.02, 502, 503, 422/504, 509; 436/43, 174, 180, 66, 68, 436/69, 63
See application file for complete search history.

(56) References Cited

U.S. PATENT DOCUMENTS

| | | | |
|---|---|---|---|
| 5,023,054 A | 6/1991 | Sato et al. | |
| 8,171,778 B2 | 5/2012 | Ayliffe | |
| 9,915,599 B2 * | 3/2018 | Brun | G01N 15/1031 |
| 2004/0077103 A1 * | 4/2004 | Buechler | B01L 3/50273 |
| | | | 436/514 |
| 2004/0115784 A1 * | 6/2004 | Dzekunov | C12M 35/02 |
| | | | 435/173.6 |

(Continued)

*Primary Examiner* — Brian J. Sines
(74) *Attorney, Agent, or Firm* — Wei Te Chung; Ming Chieh Chang

(57) ABSTRACT

An microfluidic device includes a substrate (1) having a wandering groove (12) formed on a first surface (11) thereof; a shielding member (2) abutting on the first surface and covering the groove to form a flow channel (101) to deliver blood; an inlet (14) at one end of the flow channel for introducing the blood into the flow channel; and an outlet (16) at another end of the flow channel for discharging the blood. The flow channel (101) has a detecting region (102) for the blood passing through separately, the detecting region includes an entry (1021) for a single cell entering into at a time and an exit (1022) for a single cell exiting out at a time. A pair of electrodes (211) are disposed between the entry (1021) and the exit (1022) to detect the cells (200) of the blood.

8 Claims, 10 Drawing Sheets

(56) References Cited

U.S. PATENT DOCUMENTS

| | | | |
|---|---|---|---|
| 2007/0072290 A1* | 3/2007 | Hvichia | B01L 3/502761 435/308.1 |
| 2009/0269837 A1* | 10/2009 | Shevkoplyas | B01L 3/5027 435/287.1 |
| 2010/0216126 A1* | 8/2010 | Balachandran | B01F 13/0059 435/6.11 |
| 2011/0275111 A1 | 11/2011 | Pettigrew et al. | |
| 2015/0132861 A1* | 5/2015 | Cook | B01L 3/502715 436/501 |
| 2015/0308971 A1* | 10/2015 | Bisgaard | G01N 15/12 435/29 |
| 2016/0025610 A1* | 1/2016 | Katsumoto | G01N 15/1056 435/29 |

\* cited by examiner

MICROFLUIDIC DEVICE FOR DETECTING CELLS OF BLOOD

BACKGROUND OF THE INVENTION

1. Field of the Invention

The present invention relates to a microfluidic device for detecting cells of blood.

2. Description of Related Art

Microfluidic chips are the devices used in microfluidics in which a micro-channels network has been molded or patterned, thanks to a various number of inlets and outlets, these microfluidic instruments allow fluids to pass through different channels of different diameters. Microfluidic devices such as chips have many advantages in medicine for blood analysis as they can decrease blood sample consumption and increase automation, thus minimizing analysis time, and the microfluidic devices are much portable and convenient for patients or hospitals. However, existing microfluidic devices used to comprising multiple planar layers stacked together, are still very expensive to produce because of the complicated structure.

Hence, a microfluidic device is desired to improve those disclosed in the aforementioned proposal.

SUMMARY OF THE INVENTION

According to one aspect of the present invention, a microfluidic device comprises a substrate having at least one wandering groove formed on a first surface thereof; a shielding member abutting on the first surface of the substrate and covering the groove to form a flow channel to deliver blood between the substrate and the shielding member; an inlet at one end of the flow channel for introducing the blood into the flow channel; and an outlet at another end of the flow channel for discharging the blood. The flow channel has a detecting region near the outlet for cells of the blood passing through separately, the detecting region includes an entry for a single cell entering into at a time and an exit for a single cell exiting out at a time. At least a pair of electrodes are disposed between the entry and the exit to detect the cells of the blood.

According to another aspect of the present invention, a microfluidic device comprises a substrate having at least one groove recessed from an first surface thereof; an inlet connecting to the groove for introducing the blood into the groove; an outlet connecting to the groove for discharging the blood; and a shielding member having a flat surface abutting on the first surface of the substrate and covering the groove to form a flow channel to deliver blood between the substrate. The groove has a narrowing portion small enough for cells of the blood passing through singly. The shielding member has at least a pair of electrodes formed at one side facing said substrate and disposed in an area in which the narrowing portion extending to detect the cells of the blood.

Other objects, advantages and novel features of the invention will become more apparent from the following detailed description when taken in conjunction with the accompanying drawings.

DETAILED DESCRIPTION OF THE PREFERRED EMBODIMENT

Figure 1:
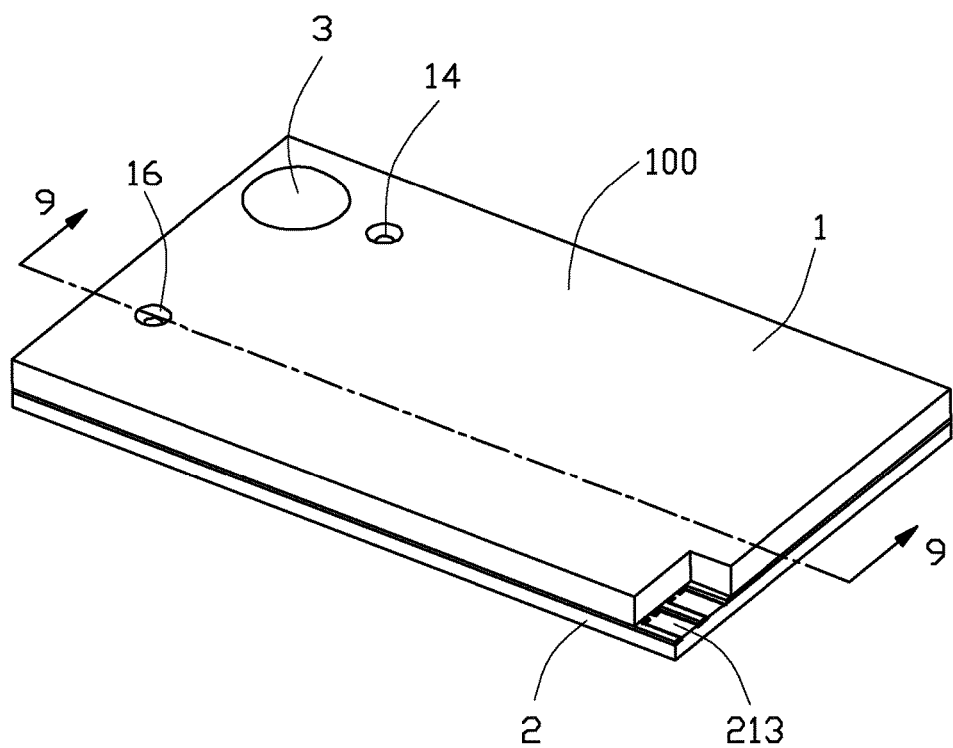
FIG. 1 is a perspective view of the microfluidic device in accordance with an embodiment of the present invention.
Figure 2:
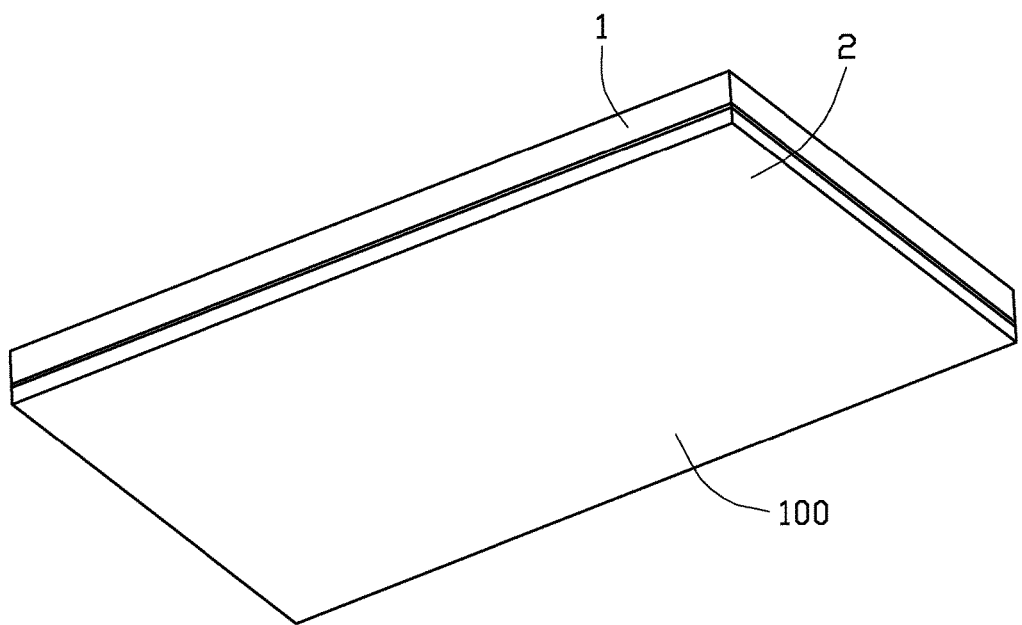
FIG. 2 is another perspective view of the microfluidic device shown in FIG. 1.
Figure 3:
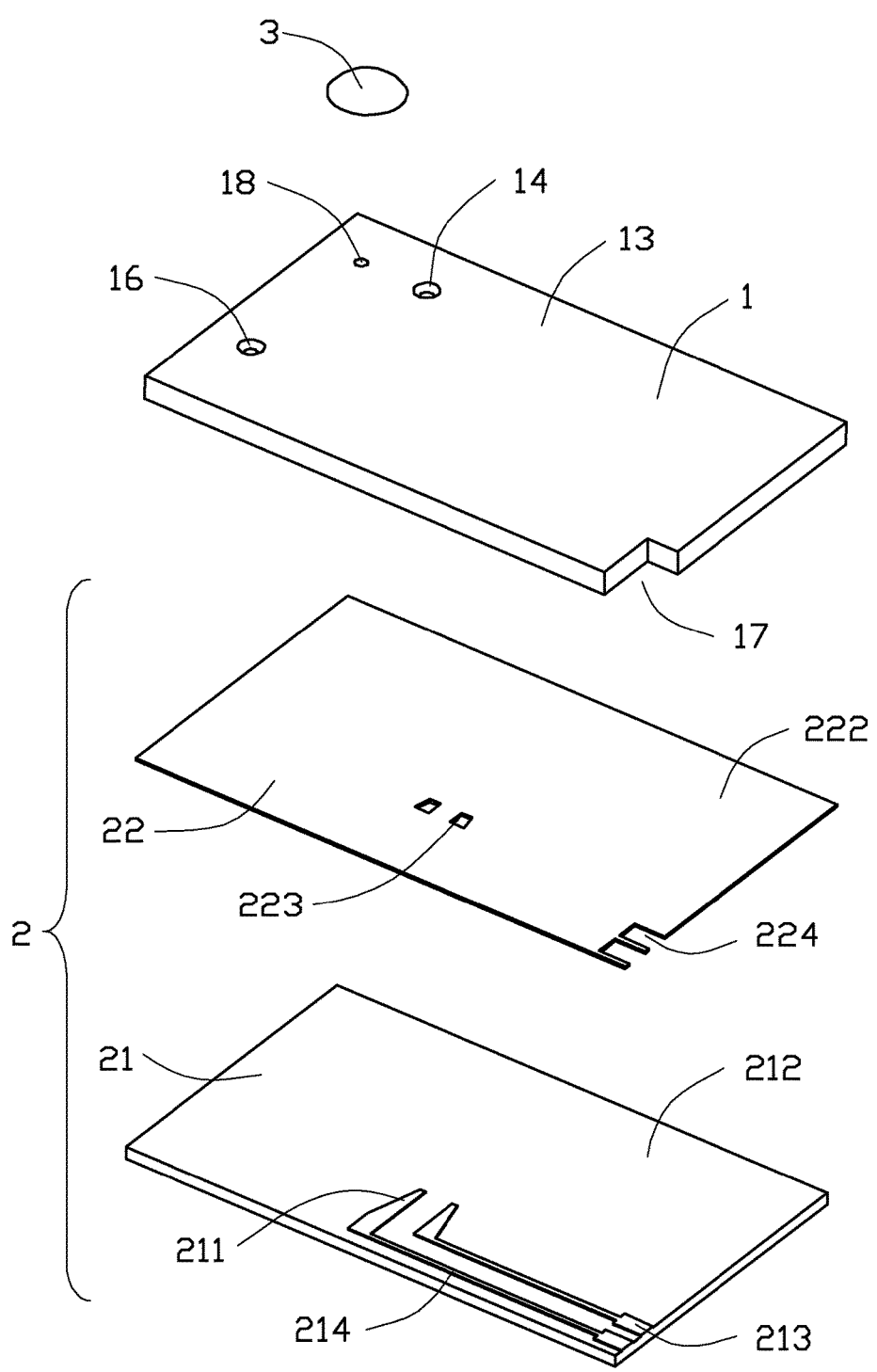
FIG. 3 is an exploded view of the microfluidic device show in FIG. 1.
Figure 4:
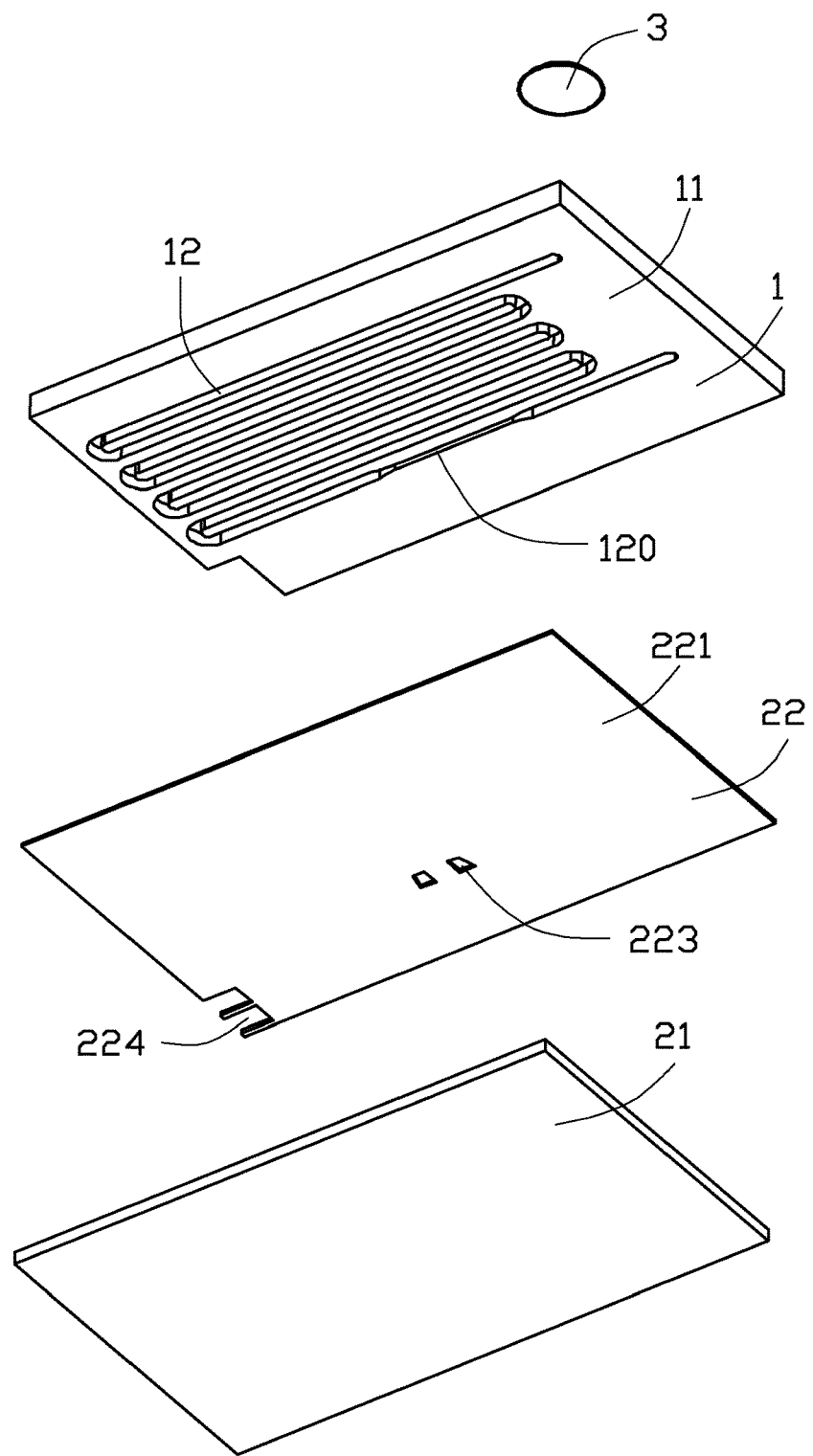
FIG. 4 is another exploded view of the microfluidic device show in FIG. 3.

Referring to FIGS. 1-4, a microfluidic device 100 according to the present invention is provided for blood cell analyses such as counting full red blood cells (RBCs) and/or white blood cells (WBCs), full blood count (FBC), CD4/CD8 white blood cell counting for HIV+ individuals, etc. The microfluidic device 100 includes a substrate 1 locating at an upper side, and a shielding member 2 locating at a lower side and attached to the substrate 1.

Figure 5:
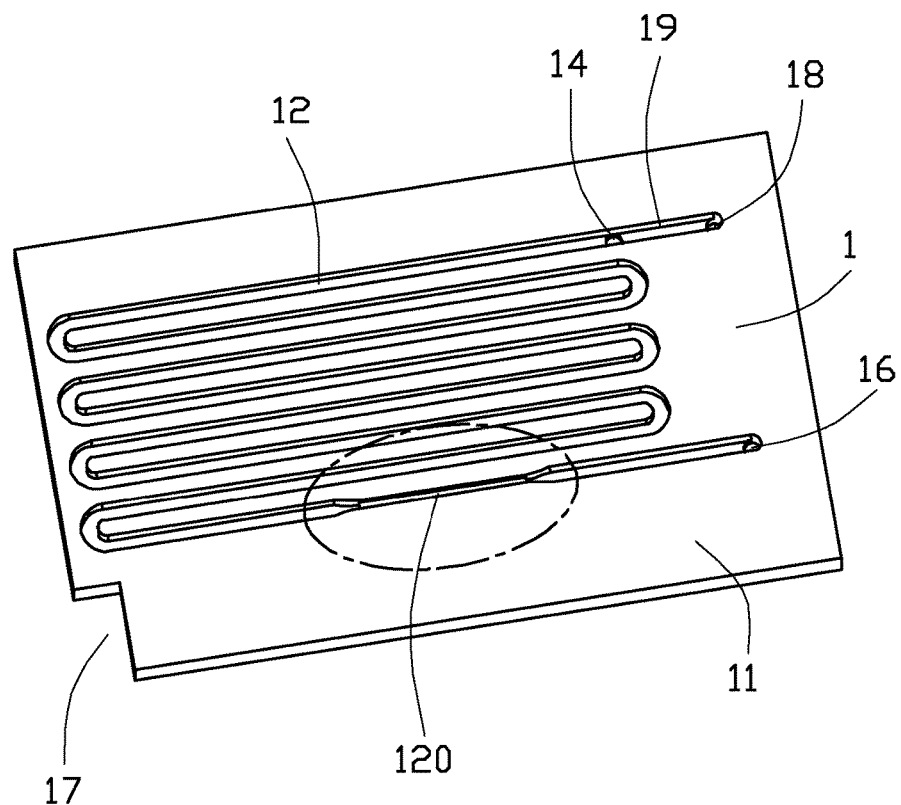
FIG. 5 is a perspective view of a substrate shown in FIG. 4.
Figure 6:
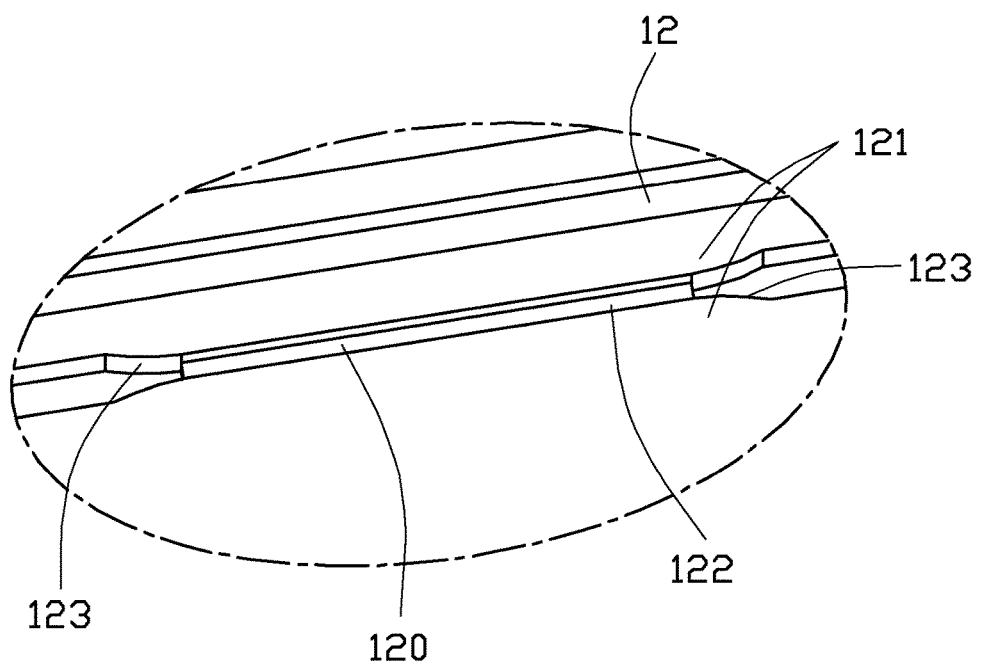
FIG. 6 is an enlarge view of a circled portion shown in FIG. 5.

Referring to FIGS. 3-6, the substrate 1 may be made of material of polydimethylsiloxane (PDMS) using injection molding. The substrate 1 has a wandering groove 12 recessed upwardly from a first surface 11 thereof at a lower side and presenting as a snake shape when viewing from the lower side. The shielding member 2 defines a substantial flat surface abutting on the first surface 11 of the substrate 1 and covering the groove 12 to form a flow channel 101 for delivering blood between the substrate 1 and the shielding member 2. The length and dimension of the groove 12 could be changed so as to adjust the time of the blood flowing in the flow channel 101.

Figure 7:
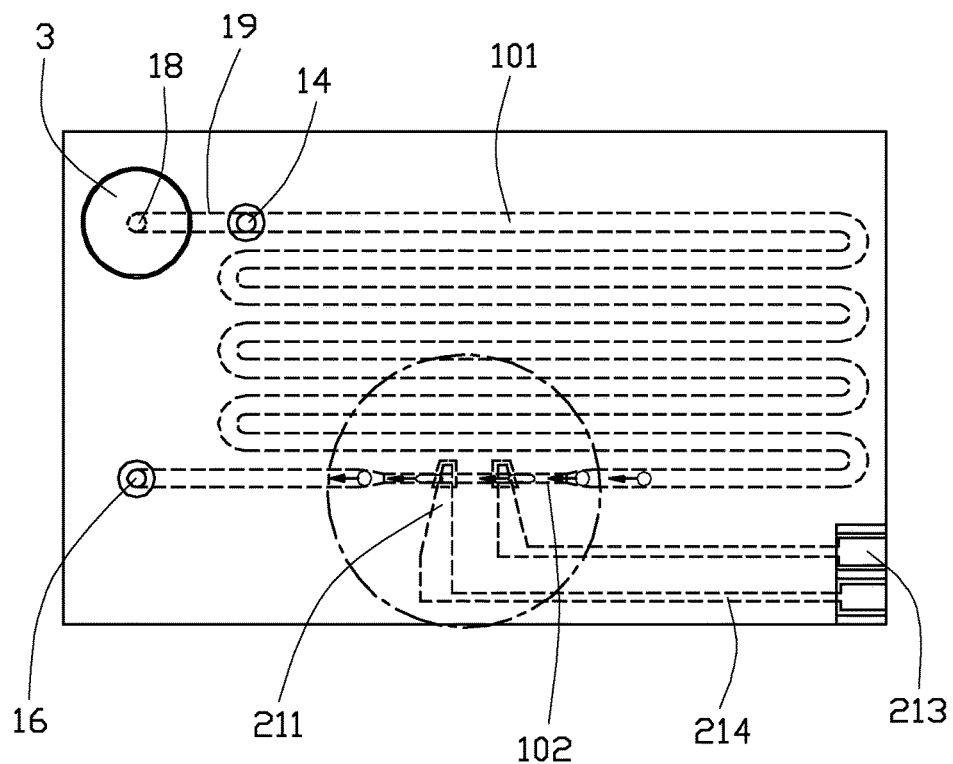
FIG. 7 is a planar schematic diagram showing the construction of the microfluidic device.

Referring to FIGS. 1-7, a tapered inlet 14 is formed on a second surface 13 of the substrate 1 opposite to the first surface 13 and disposed at the beginning of the groove 12. Said inlet 14 recesses downwardly from second surface 13 and connects to the groove 12 so as to introduce blood into the groove 12. The blood may be taken from a patient by a finger prick, because only a limited amount of the blood is required for analyzing according to the microfluidic 100 of the present invention.

A tapered outlet 16 is also formed on said second surface 13 of the substrate 1 and disposed at the ending of the groove 12. Said outlet 16 recess downwardly from the second surface 13 and connects to the groove 12 to discharge the blood. In other embodiments, a waste reservoir may be attached to the substrate 1 and disposed at the outlet 16 to collect the waste blood.

A tapered aperture 18 is formed on said second surface 13 and near the inlet 14. A passage 19 is recessed upwardly from said first surface 11 and connecting with said aperture 18 and the inlet 14. The microfluidic device 100 further comprises a push buffer 3 attached to said second surface 13 and disposed at the inlet 14, and the push buffer 3 provides lysis agent such as phosphate buffer saline (PBS). When the blood for analysis is introduced into the groove 12 via the inlet 14, press the push buffer 3, and the lysis agent is introduced into the passage 19 via the aperture 18 and delivered into the groove 12 to diffuse with the blood, therefore the rate of the blood flowing in the groove 12 will be boosted effectively.

The groove 12 which present as a snake shape has a straight narrowing portion 120 near the outlet 16 with a dimension smaller than other portions of the groove 12. Said narrowing portion 120 of the groove 12 defines a size small enough for cells 200 of the blood passing through singly or separately so that the cells 200 of the blood could be detected conveniently. The narrowing portion 120 has a pair of bumps 121 formed at two sides thereof in the width direction and protruding towards each other so as to reduce the width of the groove 12, a standoff 122 locating between the bumps 121 and protruding downwardly towards the groove 12 so as to reduce the height of the groove 12. Each of the bumps 121 has a pair of slant faces 123 formed at two sides thereof in a flow direction of the blood.

The shielding member 2 comprises a cover 21, and a double side tape 22 sticking on the cover 21. The cover 21, which also may be made of material of polydimethylsiloxane (PDMS) using injection molding, has a pair of electrodes 211 plated on an upper surface 212 thereof, and a pair of conductive pads 213 plated an corner of the upper surface 212. The conductive pads 213 electrically connect with the electrodes 211 respectively with electrical traces 214 which are also plated on the upper surface 212 of the cover. The electrodes 211 and conductive pads 213 are plated on the upper surface 212 of the cover 21 by laser direct structuring technology.

The double side tape 22 has a flat first side 221 sticking on the upper surface 212 of the cover 21 and a flat second side 222 opposite to the first side 221 sticking on the first surface 11 of the substrate 1. Therefore, the cover 21 and the substrate 1 are combined together via stickiness of the double side tape 22. The double side tape 22 has a pair of holes 223 passing therethrough in the height direction and aligning to the electrodes 211 respectively so as to expose the electrodes 211 to the narrowing portion 120 of the flow channel 101. A cutout 224 is formed on a corner of the double side tape 22 and aligns to the conductive pads 213, and the substrate 1 also has a notch 17 passing through a corner thereof and corresponding to the cutout so that the conductive pads 213 could exposes to exterior for mating.

Figure 8:
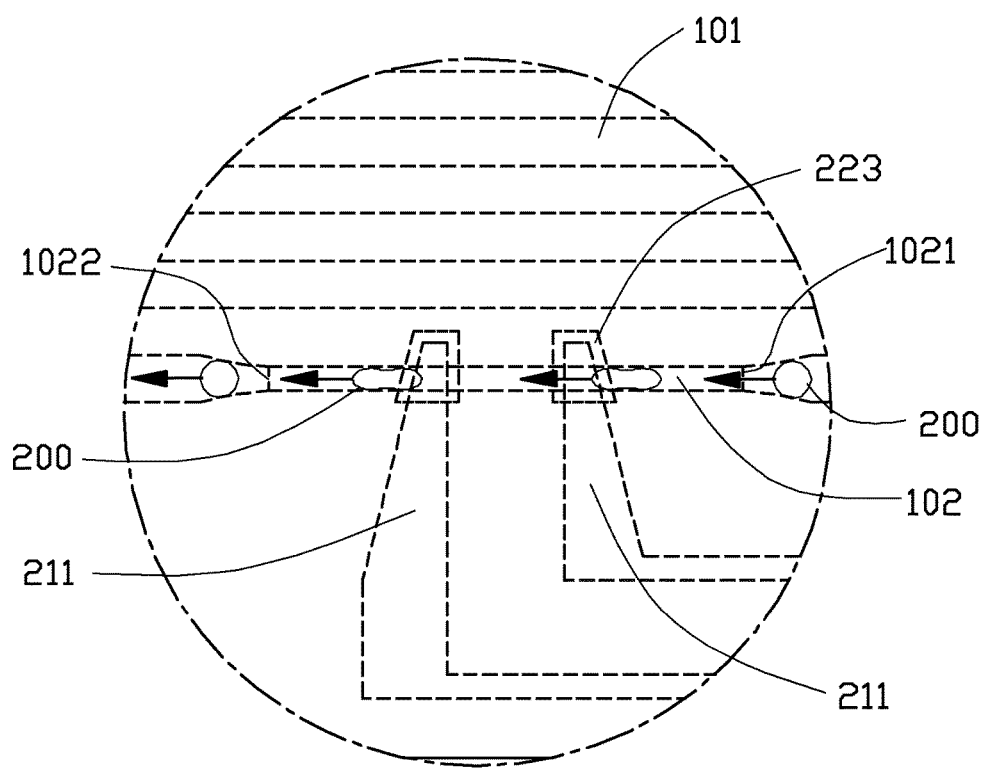
FIG. 8 is an enlarged diagram showing cells of blood passing through the detecting region shown in FIG. 7
Figure 9:
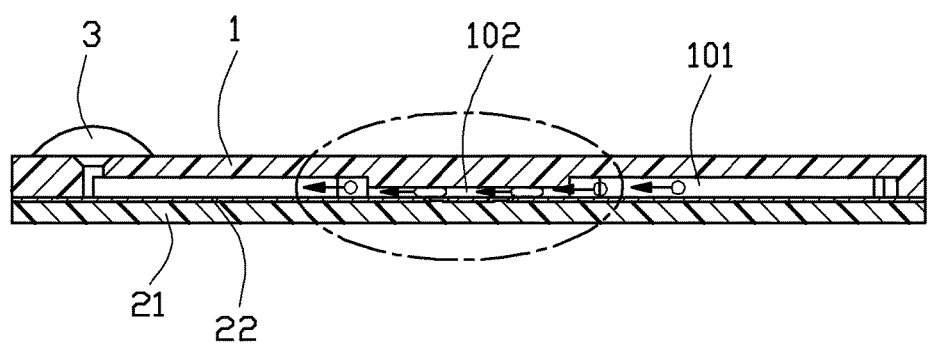
FIG. 9 is a schematic diagram of a cross-sectional view taken along line 9-9 show in FIG. 1.
Figure 10:
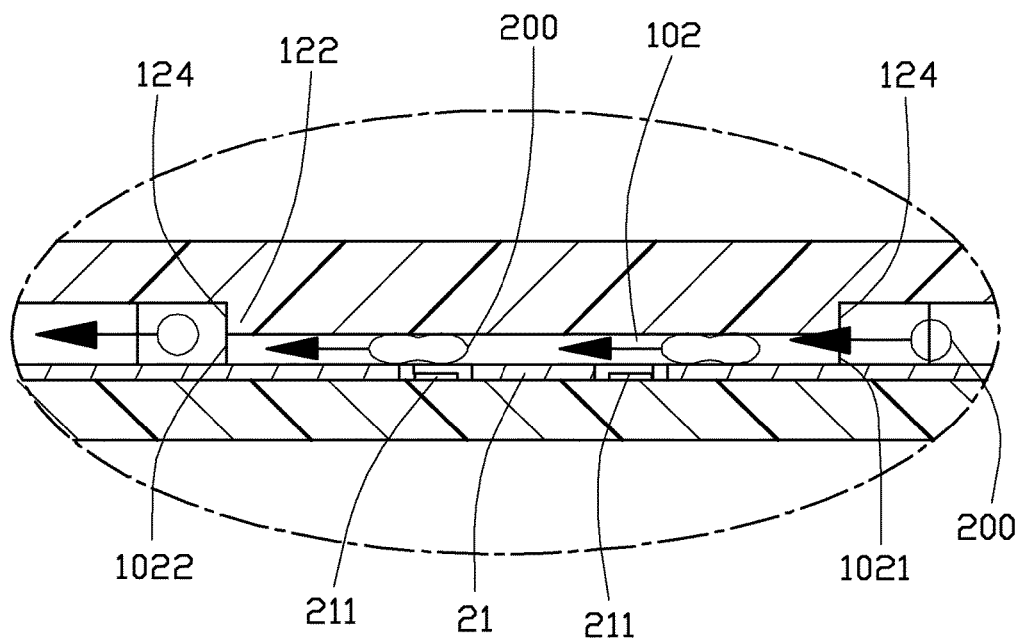
FIG. 10 is an enlarged diagram showing cells of blood passing through the detecting region shown in FIG. 9.

Referring to FIGS. 5-8, the flow channel 101 forms a detecting region 102 at the narrowing portion 120 for detecting the cells 200 of the blood. The detecting region 102 has a diameter smaller than that of each cell 200 of the blood so as to make sure the cells 200 pass through the detecting region 102 singly. The detecting region 102 defines an entry 1021 at an upstream thereof for a single cell 200 entering into at a time, and an exit 1022 at a downstream thereof for a single cell 200 exiting out at a time. Said slant faces 123 are formed at the vicinity of the entry 1021 and the exit 1022 for guiding delivery of the cells 200 smoothly. Said standoff 122 locates between the entry 1021 and the exit 1022 and further defines a pair of vertical faces 124 formed at two sides thereof in the flow direction of the blood. The electrodes 211 are disposed in the detecting region 102 and between the entry 1021 and the exit 1022, and the electrodes 211 align in a line along the flow direction of the blood. Therefore, the cells 200 of the blood passes over the two electrodes 211 successively in the detecting region, and the electrodes 211 could simply and conveniently detect whether or not any cells 200 pass through the detecting region 102, the size of the cells, and the time required for the passage of the cells, etc on basis of the resistance variations between the two electrodes 211. Furthermore, each electrode 211 strides across the detecting region 102 in the width direction of the detecting region 102 so as to detect the cells 200 reliably, each of the holes 223 also has a width lager than that of the detecting region 102. In other embodiments, various types of sensors may be disposed in the detecting region to simultaneously detect the osmotic pressure, the ion concentration, and so on, thereby achieving more precise analysis.

It is to be understood, however, that even though numerous, characteristics and advantages of the present invention have been set fourth in the foregoing description, together with details of the structure and function of the invention, the disclosed is illustrative only, and changes may be made in detail, especially in matters of number, shape, size, and arrangement of parts within the principles of the invention to the full extent indicated by the broad general meaning of the terms in which the appended claims are expressed.

What is claimed is:

1. A microfluidic device comprising:
   a substrate having at least one wandering groove formed on a first surface thereof;
   a shielding member abutting on the first surface of the substrate and covering the groove to form a flow channel to deliver blood between the substrate and the shielding member;
   an inlet at one end of the flow channel for introducing the blood into the flow channel; and
   an outlet at another end of the flow channel for discharging the blood; wherein
   the flow channel has a detecting region near the outlet for cells of the blood passing through separately, the detecting region includes a narrowed channel, an entry for a single cell entering into the narrowed channel at a time and an exit for a single cell exiting out the narrowed channel at a time; and at least a pair of electrodes are located in the narrowed channel and disposed between the entry and the exit to detect the cells of the blood;
   the shielding member comprises a cover, and a double side tape having a first side sticking on a surface of the cover and an opposite second side sticking on the first surface of the substrate; and
   the electrodes are plated on the surface of the cover using laser direct structuring (LDS) technology, and the double side tape has a pair of holes aligning to the electrodes respectively to expose the electrodes to the detecting region of the flow channel.

2. The microfluidic device as claimed in claim 1, wherein the cover has a pair of conductive pads plating at an end of the surface and electrically connecting with the electrodes, the double side tape has a cutout aligning to the conductive pads, and the substrate has a notch passing therethrough in a height direction and corresponding to the cutout for exposing the conductive pads to exterior.

3. The microfluidic device as claimed in claim 1, wherein the electrodes align in a line along a flow direction of the blood, and each electrode strides across the detecting region of the flow channel in a width direction of the detecting region.

4. The microfluidic device as claimed in claim 1, wherein the detecting region of the flow channel has a diameter smaller than the diameter of each cell of the blood.

5. The microfluidic device as claimed in claim 1, wherein both the inlet and the outlet are formed on a second surface of the substrate opposite to the first surface and connecting to the groove in a height direction of the substrate.

6. The microfluidic device as claimed in claim 5, wherein the substrate further has an aperture formed on the second surface and locating at the vicinity of the inlet, a passage connecting with the aperture and the inlet; the microfluidic device further comprise a push buffer attached to the second surface of the substrate and engaging with the aperture to introduce a lysis agent into the passage for diffusing with the blood.

7. The microfluidic device as claimed in claim 1, wherein the groove has a narrowing portion at the detecting region to form the narrowed channel of the flow channel and defining a size small enough for the cells of the blood passing through separately.

8. The microfluidic device as claimed in claim 7, wherein a pair of bumps are formed in the narrowing portion and protrude towards each other in the width direction, and a standoff is formed in the narrowing portion protrudes upwardly towards the groove; each bump has a pair of slant faces formed at the vicinity of entry and exit respectively, and the standoff has a pair of vertical faces formed at the entry and exit respectively.

\* \* \* \* \*